United States Patent [19]

Naylor et al.

[11] 4,149,527

[45] Apr. 17, 1979

[54] PACEMAKER ARTIFACT SUPPRESSION IN CORONARY MONITORING

[75] Inventors: Thomas K. Naylor, Belmont; Alan S. Cushing, Milton, both of Mass.

[73] Assignee: American Optical Corporation, Southbridge, Mass.

[21] Appl. No.: 781,816

[22] Filed: Mar. 28, 1977

[51] Int. Cl.² ............................................. A61B 5/02
[52] U.S. Cl. ............................................. 128/2.06 B
[58] Field of Search .................. 128/2.06 B, 2.06 G, 128/2.06 R, 2.06 F, 2.05 T, 419 PT, 2.06 A; 328/162, 165, 163, 115, 116

[56] References Cited

U.S. PATENT DOCUMENTS

| | | | |
|---|---|---|---|
| 3,374,435 | 3/1968 | Engel | 328/165 |
| 3,674,015 | 7/1972 | Berkovits | 128/2.06 F |
| 3,923,041 | 12/1975 | Stasz et al. | 128/2.06 R |
| 3,986,496 | 10/1976 | Brastad | 128/2.06 R |
| 4,000,461 | 12/1976 | Barber et al. | 128/2.05 A |

Primary Examiner—Robert W. Michell
Assistant Examiner—Arthur S. Rose

Attorney, Agent, or Firm—Jeremiah J. Duggan; Howard R. Berkenstock, Jr.; Stephen A. Schneeberger

[57] ABSTRACT

In cardiac signal processing apparatus, there is provided improved means for suppressing pacer signal artifacts, including both the discharge pulse and the recharge waveform (tail) of such artifact. Rate-limiting circuitry is used to substantially suppress the discharge pulse. However additional circuitry responsive to the detection of a pacer pulse is operative to obtain a measure of the electrical discharge of the discharge portion of the respective pacer pulse and to use such measure to generate a tail suppression signal which, when added to the original signal, substantially cancels the original pacer tail.

A feed-back loop is opened by the rate-limiter when a pacer pulse occurs and in turn permits a large signal to be imposed on a threshold-level-type pacer pulse detector for connecting the large signal (pacer pulse) to a capacitor during the discharge portion of the pacer pulse. The capacitor begins to discharge shortly after the pacer pulse's discharge portion with a polarity and time constant selected to substantially cancel (when summed) the pacer tail.

20 Claims, 12 Drawing Figures

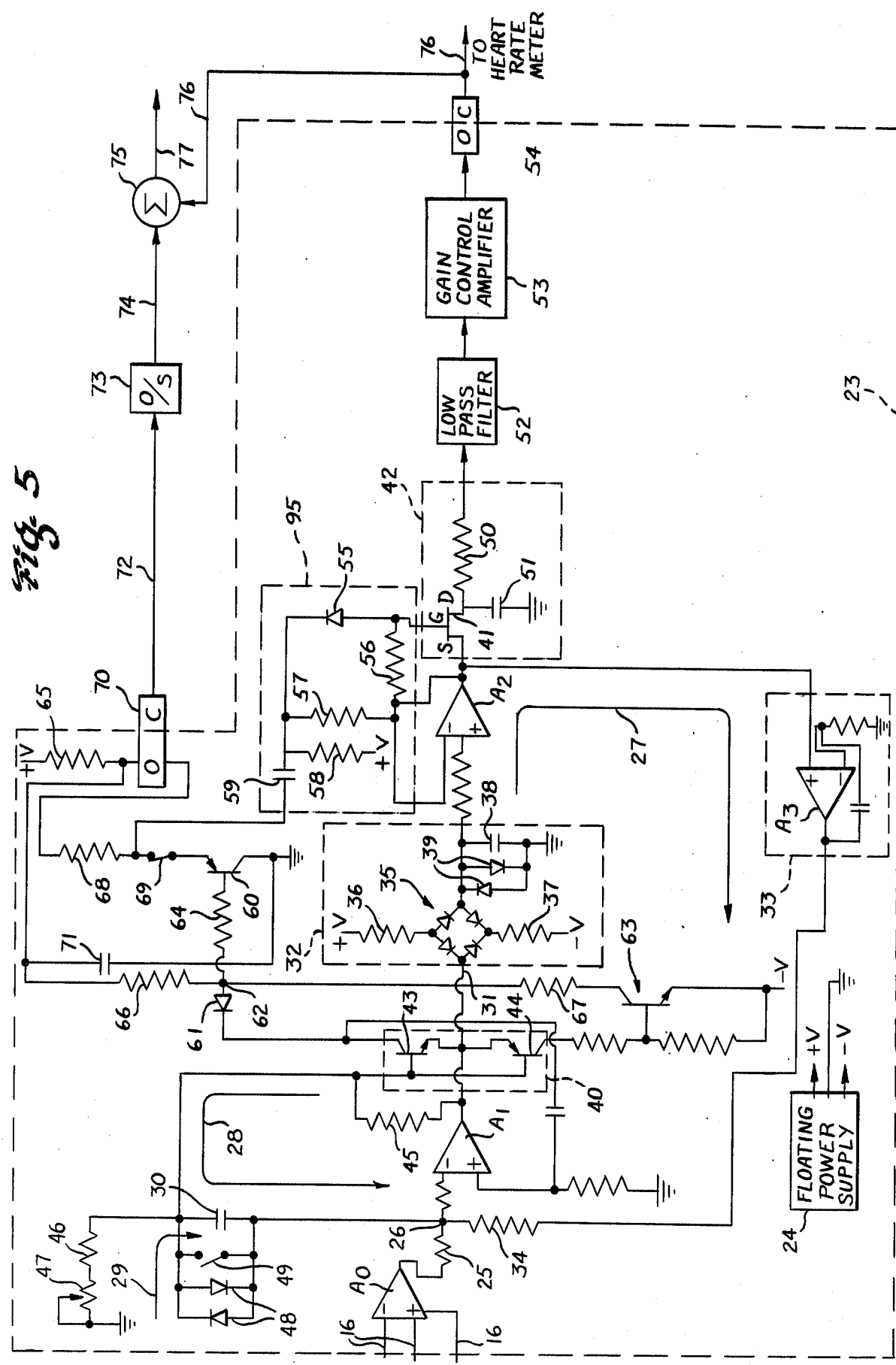

IMPROVED PACEMAKER ARTIFACT SUPPRESSION IN CORONARY MONITORING

BACKGROUND OF THE INVENTION

The invention relates generally to heart-monitoring systems and more particularly to the improved suppression of pacemaker artifacts appearing in ECG signals.

In the art of heart-monitoring, thoracic electrical potentials of the patient are sensed to provide an input signal to amplifying means which amplify and process the signal for application to various utilization devices including recorders, CRT displays, heart-rate indicating means, and the like. In the particular instance of heart-rate monitoring, the heart-rate indicator is normally responsive only to sensed signals which correspond in frequency and amplitude substantially with the QRS complex or the R wave of a natural heart beat appearing in the ECG. However, in the event the patient is receiving artificial stimulation as by a heart pacemaker, the sensed electrical signals resulting directly from the pacer may additionally introduce artifact signals having amplitudes and/or frequencies which may be inaccurately identified as a naturally occurring heart rhythm and, in the worst case, may provide an indication of continuing heart activity when, in fact, heart activity has ceased and the patient is technically dead. This erroneous determination that a pacer signal artifact constitutes a normal QRS complex may be made not only by heart-rate indicating means, but also by other analytical means including human observers. For this reason, it is important to suppress pacer signal artifacts which might otherwise be misinterpreted as a functioning of the heart.

The pacer signal artifact normally comprises a stimulation pulse portion, or "spike", representative of the discharge of capacitively-stored electrical energy into the patient's heart and generally also a recharge waveform portion or "tail" attending the recharge of the pacer's energy-storing capacitor.

The prior art has provided various circuit means for suppressing the "spike" portion of the pacer signal artifact, usually by preventing transmission of the sensed signal to the utilization circuitry for the duration of the pacer discharge pulse. Such circuits have, however, generally been relatively complex and/or subject to drift and/or muscle noise or artifact.

Recently, means have been provided for also suppressing the pacer recharge waveform or "tail", as described in greater detail in U.S. application Ser. No. 760,487 for PACEMAKER ARTIFACT SUPPRESSION IN CORONARY MONITORING BY Marchese et al., filed Jan. 19, 1977, now U.S. Pat. No. 4,105,023 and which is incorporated herein by reference to the extent consistent herewith. Briefly, the "tail" suppression circuitry of the aforementioned application utilizes a differentiating circuit to recognize the occurrence of a pacer pulse and to control the timing of an interval associated with pacer recognition circuitry such that immediately following the end of the "spike" portion of a recognized pacer signal artifact, the pacer "tail" portion is sampled and the amplitude of the sample is utilized for generating a "tail" suppression signal of opposite polarity to the "tail" portion of the pacer signal artifact. The "tail" suppression signal is arithmetically added with the ECG signal containing the pacer signal artifact such that the pacer "tail" portion thereof is reduced in amplitude and substantially cancelled, thereby avoiding the possibility of its actuating rate-indicating circuitry or the like.

Regarding the prior technique and circuitry for suppressing the "tail" portion of the pacer signal artifact as disclosed in the aforementioned U.S. patent application, it will be appreciated that generation of the "tail" suppression signal required an amplitude measurement to be made of the "tail" immediately following termination of the "spike" portion of the pacer signal artifact. In order to accomplish this, it was first necessary to determine that a high frequency signal in the sensed ECG was indeed a pacer artifact signal and subsequently to accurately identify the brief interval during which the amplitude of the "tail" is to be sampled. The circuitry employed for such technique tends to be complex.

Accordingly, it is a principal object of the present invention to provide an improved means for the suppression of pacer signal artifact in a heart-monitoring system. Included in this object is the provision of means for preventing false actuation of heart-rate indicating means by any portion of a heart pacer signal artifact.

It is a further object of the present invention to provide improved means for suppressing the recharge waveform portion of a pacer signal artifact appearing in a sensed ECG signal. Included in this object is the provision of relatively simple, reliable and low-cost means for the suppression of the recharge waveform portion of a signal artifact.

It is a still further object of the present invention to provide improved pacer signal artifact suppression means with minimal response to muscle artifact.

It is an even further object of the present invention to provide improved means for the suppression of the discharge pulse portion of a pacer signal artifact.

These and other objects will be in part obvious and in part pointed out in greater detail hereinafter.

SUMMARY OF THE INVENTION

One aspect of the invention recognizes that the electrical recharge of a pacer is equal and opposite to its heart-stimulating electrical discharge. By measuring the latter and knowing approximately the time-constant of the former, it is possible to generate an approximate recharge suppression signal.

In accordance with the principles of the invention, there is provided, in a heart-monitoring system for receiving a sensed ECG signal from a patient and including means for suppressing the pacer discharge pulse portion and the recharge waveform portion of a heart pacer signal artifact possibly appearing in the sensed ECG signal, improved signal suppression means comprising means responsive to the pacer discharge pulse portion of a pacer signal artifact in the sensed ECG signal for providing a measure of the electrical discharge of the respective discharge pulse portion, said measure of discharge being representative of the electrical recharge of the recharge waveform portion of the respective pacer signal artifact; means responsive to said measure of electrical discharge for generating a recharge waveform suppression signal of opposite polarity to the recharge waveform portion of the pacer signal artifact; and means for arithmetically summing the recharge waveform suppression signal with the recharge waveform portion of the pacer signal artifact, the magnitude and time constant of the recharge waveform suppression signal being scaled to reduce and/or substantially cancel the recharge waveform portion of the pacer signal artifact.

In a preferred embodiment, the means for obtaining a measure of the pacer electrical discharge comprises integrating a signal proportional to the voltage of the discharge pulse portion of a pacer signal artifact utilizing an operational amplifier having an input and an output, the sensed ECG signal being connected to the amplifier input, and energy-storing means connected in a local feedback loop between the output and the input of the operational amplifier at least for the interval during which a pacer discharge pulse portion exists for integrating the sensed ECG signal applied to the operational amplifier input, the integral of the ECG signal over the interval of pacer discharge pulse portion existence being a measure of the pacer electrical discharge of the respective pacer discharge pulse portion.

Further, the recharge waveform suppression signal generating means comprises means for utilizing the energy stored by the storing means during the integration to generate a suppression current of decreasing magnitude substantially immediately following the discharge pulse portion of the pacer signal artifact, the initial magnitude and the rate of decay of the suppression current being determined by a resistance-capacitance circuit to which the stored energy is applied, the suppression current being extended to the operational amplifier input and being of the opposite polarity to the current of the recharge waveform signal portion of the sensed ECG signal applied to the operational amplifier input thereby to have a mutually cancelling effect. The capacitance of the aforementioned resistance-capacitance circuit may also comprise part of the feedback loop so as to provide the energy-storing or integrating means.

The aforementioned feedback loop including the energy-storing means is normally disconnected from significant feedback relationship with the operational amplifier and is selectively controllable for connection into significant feedback relationship therewith, the feed-back arrangement including controllable, normally-open switch means in series with the energy-storing means and being responsive to the output of the operational amplifier exceeding a predetermined amplitude level for connecting the feedback arrangement in significant feedback relationship with the operational amplifier.

A second feedback loop is normally operatively connected between the output and input respectively of the operational amplifier for providing negative feedback to the operational amplifier input to limit the amplitude of the signal appearing at the output thereof to values normally less than the predetermined amplitude level required for response of the switch means. The second feedback loop includes rate-limiting means and second integrating means, the former serving to effectively disconnect the loop when a predetermined rate-of-amplitude change of the sensed ECG signal is exceeded to allow the operational amplifier output signal to exceed the predetermined amplitude level required for response to the switch means and the latter being utilized to minimize or eliminate DC offset in the operational amplifier's output signal.

The normally-open switch means may comprise a pair of oppositely-poled, parallel-connected, complementary transistors connected between the output of the operational amplifier and the energy-storing means. A resistor of relatively large ohmic value connected in parallel with the transistor switches serves to minimize the appearance of noise in the signal from the operational amplifier when both transistors are non-conducting and the first or local feedback loop is essentially opened.

According to a further aspect of the invention, improved suppression and/or rejection of the pacer pulse portion, as well as the brief initial portion of the "tail", is provided by gated follow and hold circuitry which passes or blocks passage of a tentative output signal appearing at a selected point in the aforementioned feedback loop. Preferably, the tentative output signal is obtained at the output of the rate-limiting means, which output may be undesirable during rate-limiting. Signal level detection means respond to the signal at the output of the operational amplifier exceeding a predetermined threshold occurring only during rate-limiting to control the follow and hold means such that it blocks passage of the tentative output signal during that interval.

BRIEF DESCRIPTION OF THE DRAWINGS

FIG. 5 is a schematic diagram of the ECG amplifier including the pacer signal artifact suppression circuitry of the heart-monitoring system of FIG. 1.

DESCRIPTION OF THE PREFERRED EMBODIMENTS

Figure 1:
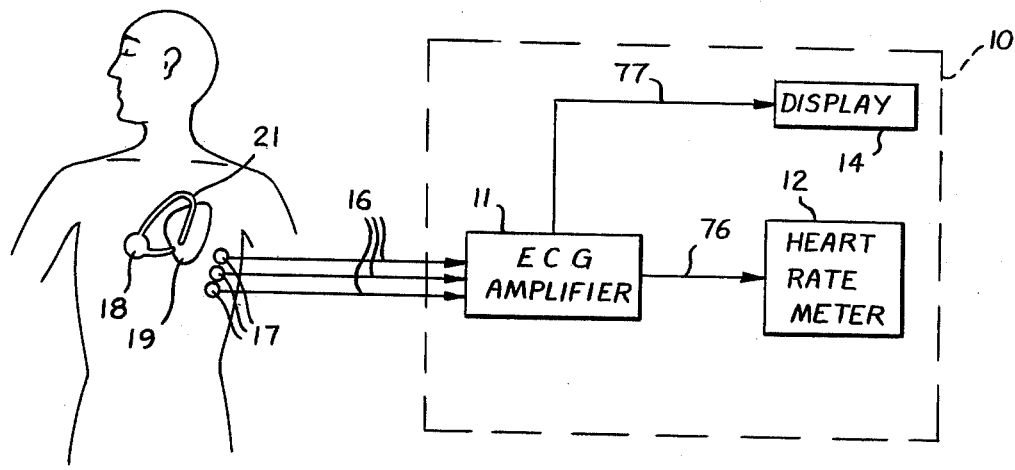
FIG. 1 is a diagrammatic representation of the heart-monitoring system of the invention operatively connected to a patient having an implanted heart pacer.

Referring to FIG. 1, there is illustrated a heart-monitoring system 10 comprised of an ECG amplifier 11, a heart-rate meter 12, and display 14 which may be a CRT and/or a permanent recorder. The monitoring system 10 and more specifically the ECG amplifier 11, is electrically connected to a patient 15 via a plurality of conductors 16 connected with respective electrodes 17 in contact with, and appropriately positioned on, the skin of the patient. FIG. 1, being merely diagrammatic, does not necessarily represent optimum positioning of electrodes 17.

Figure 2:
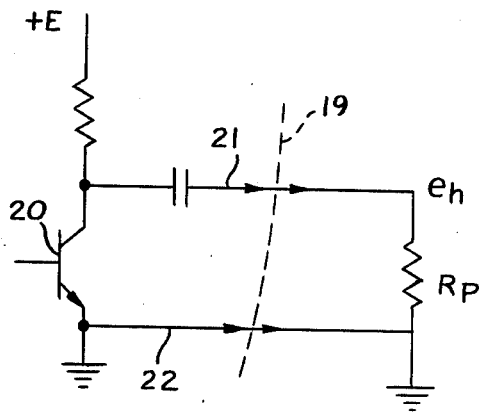
FIG. 2 depicts the output circuit of the heart pacer including the impedance of the patient.

Patient 15 is illustrated as having an implanted pacer 18 connected in operative heart-stimulating relation with his heart 19. Typically the output circuitry of pacer 18, as illustrated in FIG. 2, includes a capacitor, C, connected through a resistor, R, to a source of voltage, +E, and connected at its other end to a heart electrode 21 which is operatively disposed within or adjacent to heart 19. Another electrode 22 of the pacer 18 is also operatively connected to the heart 19 and serves as a circuit reference or current return path. The patient 15 represents an impedance $R_p$ between the electrodes 22 and 21. Capacitor C charges through the circuit comprising patient impedance $R_p$, capacitor C and resistor R. A switching transistor 20 having a grounded emitter and having its collector connected to resistance R and capacitor C is switched into conduction for discharging the energy stored in capacitor C into the heart 19 to provide stimulation in a known manner.

Figure 4:
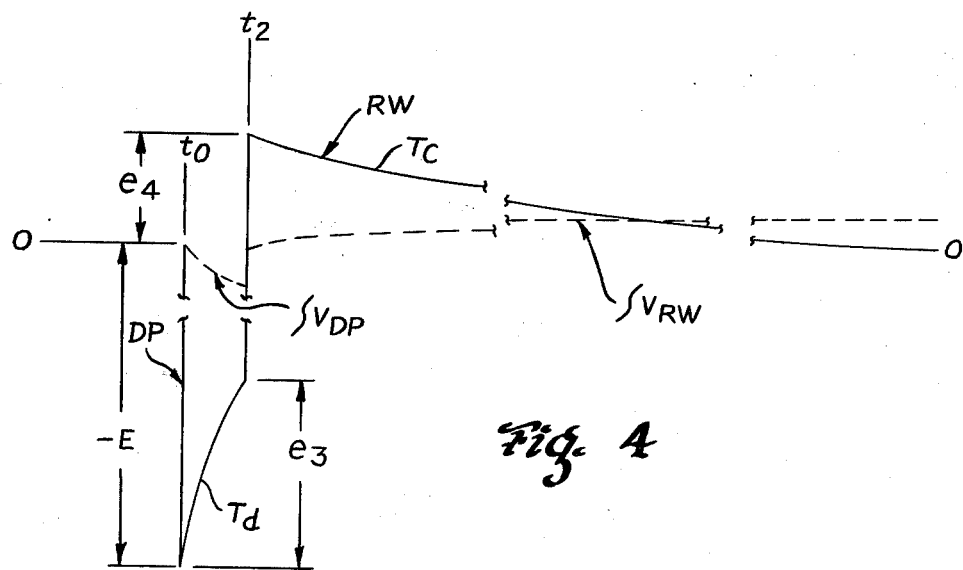
FIG. 4 is an enlarged partial view of FIG. 3 showing a sensed pacer signal artifact in greater detail.

FIG. 4 represents the waveform of the voltage $e_h$ appearing at electrode 21 of pacer 18 in FIG. 2 during and following the generation of a pacer discharge or stimulation pulse ("spike") DP. Capacitor C is assumed to be charged to voltage $+E$ prior to the occurrence at time $t_o$, of a control signal of duration $T_w$ on the base of transistor 20. The control signal (not shown) controls the time during which energy is discharged to the heart 19 and typically may be about 0.5–3 msec., with 2 msec. being selected for the purposes of illustration herein. At $t_0$ transistor 20 conducts, immediately dropping the voltage at electrode 21 by the magnitude E. The capacitor C then begins to discharge through the heart with a time constant $T_d$ which is the product of capacitor C and the patient impedance $R_p$. At the end of 2 msec. (i.e. $t_2$), normally prior to complete discharge of capacitor C, transistor 20 is turned off and the capacitor C begins to recharge with the time constant $T_c$ being equal to (R + $R_p$) C, where R is known and generally many times larger than $R_p$.

It will be noted in FIG. 4 that when the discharge pulse DP terminates at $t_2$ (2 msec.), the voltage on pacer electrode 21 moves positively beyond the normal zero reference level and experiences an overshoot voltage $e_4$ which is determined by the relationship $e_4 = (e_3 R_p)/(R + R_p)$, where $e_3$ is the magnitude of voltage decay during discharge of capacitor C. Typically, the magnitude of voltage E may be 6 volts, $R_p$ might be about 500 ohms, R may be about 25 kilohms, $e_3$ may be several volts, and the magnitude of the overshoot $e_4$ may be about 1/40 of that, or in the range of 25–150 MV. The recharge time constant $T_c$ may be 200–300 msec. such that capacitor C is not substantially fully recharged for possibly 500 msec. or more. Accordingly, it will be appreciated that the pacer recharge waveform RW, or so-called pacer "tail", may have a magnitude greater than 100 MV at the heart for many 10's of milliseconds and even more than 100 msec.

Important to the invention, as will later become evident, is the fact that the electrical recharge of capacitor C is equal and opposite to its electrical discharge. The charge (or discharge) is proportional to the integral of the voltage with time, assuming a constant capacitance. Thus, in FIG. 4, the integral of the spike ($SV_{DP}$) provides a measure of the discharge and the integral of the tail ($SV_{RW}$) provides a measure of the recharge, the two being equal and opposite at the end of their respective pacer signal portions.

Figure 3:
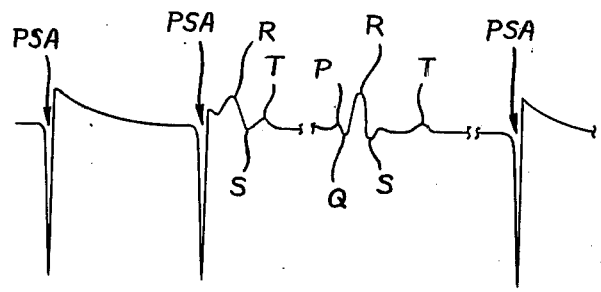
FIG. 3 represents the sensed thoracic voltage waveform of a patient having a pacemaker and includes sensed pacer stimulation pulses and PQRST complexes of the heart.

Although the magnitude of the pacer discharge pulse DP and the recharge waveform RW are substantially attenuated when sensed by electrodes 17 at the skin of patient 15, the electrical signals attendant normal heart functioning and represented by the PQRST complex of FIG. 3 are similarly attenuated such that the pacer discharge pulse DP is normally many times larger than any part of the PQRST complex and the recharge waveform RW may have an initial magnitude comparable to or greater than the R-wave portion of the complex. Furthermore, the general frequency characteristics of the recharge waveform RW are comparable to those exhibited by a normal QRS complex. For these reasons, the pacer discharge pulse DP and/or the recharge waveform RW may jointly or separately appear as normal QRS complexes to the R-wave detection circuitry of heart-rate meter 12, as well as to someone monitoring the display 14.

Referring briefly to FIG. 3, the displayed waveform illustrates the signal sensed by electrode 17 at the skin of patient 15 and provided as an input signal to amplifier 11 of the monitoring system 10. The left-most perturbation in the signal is designated PSA for Pacer Signal Artifact and includes the discharge pulse portion DP and the recharge waveform portion RW of a pacer pulse. This particular PSA was not successful in achieving capture of the heart. The next-rightward perturbation shows a pacer signal artifact PSA which was successful in achieving capture of the heart, thus resulting in the stimulated generation of the Q (not seen) RST complex by the heart within about 100 msec. after the pacer pulse. Next rightward, there is illustrated a complete, natural PQRST complex of the heart, without a PSA signal inasmuch as pacer 18 is of the demand type. Finally, there is a repetition of a pacer signal artifact PSA which is unsuccessful in achieving capture of the heart.

The heart rate meter 12 possesses magnitude and frequency discriminating circuitry of a generally known type for recognizing the R-wave in the ECG signal and recording or indicating such as evidence of a heart beat. However, that circuitry of meter 12 may also respond to the discharge pulse DP and/or the recharge waveform RW of the pacer signal artifact PSA to additionally register a heart beat, when, in fact, no heart beat may be present. Accordingly, circuitry associated with amplifier 11 is operative to suppress not only the discharge pulse DP but also the recharge waveform RW in accordance with the invention to prevent their falsely actuating the rate meter 12. It will be appreciated that while the pacer signal artifact suppression circuitry to be hereinafter described is preferably associated with amplifier 11, at least a portion of it might be "packaged" as part of the rate meter 12.

Figure 6A:
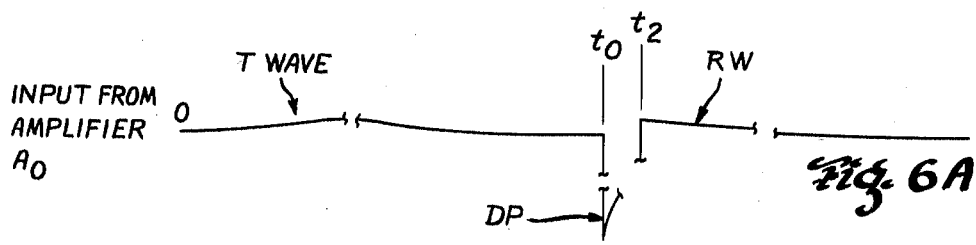
FIGS. 6a-6g comprise a waveform ladder diagram showing the time and amplitude relationships of various waveforms throughout the ECG amplifier of FIG. 5.

In the illustrated embodiment, the circuitry for suppressing the pacer signal artifact is provided in the ECG amplifier 11, shown in greater detail in FIG. 5. Most of the circuitry of amplifier 11 is isolated, as represented by the dotted line 23 in FIG. 5, to prevent the flow of dangerous currents between the patient and the remaining circuitry such as rate meter 12 and/or display unit 14. A floating power supply 24 provides the requisite operating potentials for the isolated section of amplifier 11 and includes a floating reference potential (illustrated as 1 ), $+V$ (i.e. $+15$ volts), and $-V$ (i.e. $+15$ volts). The $+$ and $-V$ power supply potentials are extended to the various differential amplifiers and related circuitry of ECG amplifier 11 by conductors omitted from the illustration. The leads 16 from the patient comprise inputs to the differential preamplifier $A_0$ which develops and initially amplifies the basic ECG input signal to amplifier 11. Amplifier $A_0$ may typically have a gain of about fifteen (15) and further has a one kHz bandwidth for attenuating high frequency noise. The preamplified signal appearing at the output of amplifier $A_0$ is extended through input resistor 25 to input junction 26 which is connected to the inverting input of an operational amplifier $A_1$. The input signal to amplifier $A_1$ from the patient via preamplifier $A_0$ and resistor 25 is illustrated in FIG. 6A and includes a T-wave at the end of a PQRST complex and a pacer signal artifact. It will be appreciated that the duration of the T-wave is many, many times that of the spike portion of the pacer artifact.

The non-inverting input to operational amplifier $A_1$ is normally connected to a reference potential such that the amplifier inverts the input signal illustrated in FIG. 6A. The inverting amplifier $A_1$ is provided with a general feedback loop designated by arrow 27 for providing degenerative or negative feedback to the input thereof and a local, negative feedback loop also connected to the input thereof and designated by the arrow 28. The feedback loops, as represented by arrows 27 and 28, generally operate in a complementary nature to one another with the general feedback loop 27 providing significant feedback in the presence of normal ECG signals except during the early interval of a pacer signal artifact, and the feedback loop 28 providing significant feedback essentially only during the interval in which loop 27 does not provide significant feedback. The term "significant" as applied to feedback loops 27 and 28 herein is used to distinguish operation of those feedback loops in their conventional feedback mode from that mode approximating an open loop condition in which little or no feedback is provided.

In addition to the normal ECG signal input from amplifier $A_0$ and the complementary inputs from feedback loops 27 and 28, the amplifier $A_1$ also receives at junction 26 an input comprising a recharge waveform suppression signal developed over the path designated by arrow 29. In fact, the recharge waveform suppression signal path represented by arrow 29 operates in time-succession with the provision of negative feedback via the feedback loop represented by arrow 28, both having an energy-storing capacitor 30 in common therewith for the purpose to be hereinafter explained.

The output of amplifier $A_1$ is extended via line 31 to a rate limiter 32, the output of which is extended to the non-inverting input of an amplifier $A_2$. The general negative feedback loop (represented by arrow 27) for amplifier $A_1$ is completed by extending the signal appearing at the output of amplifier $A_2$ through a low frequency rejection circuit or integrator 33 and thence through resistor 34 to the junction 26 at the input of amplifier $A_1$.

The rate limiter 32 serves a dual function, that of partially suppressing the discharge pulse portion of a pacer signal artifact and possibly the more important function of essentially opening the feedback loop 27 throughout the interval of the pacer discharge pulse portion and continuing for a like interval thereafter. The rate limiter 32 is of conventional design and includes a four-diode bridge having a resistor 36 connected from the positive supply of voltage to the common anodes of two legs of the bridge and a resistor 37 connected from the negative supply of voltage to the common cathodes of the other two legs of the bridge. Conductor 31 is connected to apply the output of amplifier $A_1$ to one cathode-anode junction of bridge 35, the other cathode-anode junction thereof being connected to one side of a capacitor 38 which has its other side connected to the reference potential.

The values of resistors 36 and 37 are identical and form complementary current sources to the bridge 35 and ultimately to capacitor 38. The magnitude of current supply to the capacitor 38 is controlled by the amplitude of the signal appearing on 31 up to a maximum current determined by the values of the resistors 36 and 37. In the present embodiment, the values of resistors 36 and 37 (91k ohm) and the value of capacitor 38 (10M$^{fd}$) are selected such that the maximum rate at which the voltage on capacitor 38 may vary is limited to some predetermined value. In the present instance, that value is 1 volt per second referred to the input of amplifier 11 (i.e. about 15 volts per second at capacitor 38).

The voltage on capacitor 38 is thus able to accurately follow the voltage excursions on line 31 for signal slew rates which are less than the predetermined rate limit, but is limited by the predetermined rate-limit value for signal excursion rates which exceed that limit. The rate-limit value is selected to pass those signals appearing on line 31 having frequency characteristics commensurate with either the normal PQRST complex of an ECG signal or the myoelectric artifacts commonly referred to as muscle noise, and to rate-limit for higher signal slew rates which are characteristic of the discharge pulse portion of a pacer signal artifact. By not rate-limiting for muscle noise, the circuitry is prevented from generating an undesired recharge waveform suppression signal. The maximum amplitude of voltage excursion appearing on capacitor 38 is limited during overload (i.e. to one-half volt) by a pair of oppositely-poled diodes 39 in parallel therewith. The output from rate-limiter 32 during the occurrence of a pacer signal artifact is illustrated in FIG. 6D wherein it is observed that throughout the duration of the discharge pulse portion of the signal (i.e. $t_0$–$t_2$), the rate-limiter output increases at a constant, rate-limited slope and following conclusion of the discharge pulse portion the rate-limited output drops at its maximum rate, that rate having the same magnitude of slope as the increasing rate but in the opposite or negative direction and continuing for a like interval (i.e. $t_2$–$t_4$).

The low-frequency rejection circuit 33 is an integrator comprised of operational amplifier $A_3$ with the output of amplifier $A_2$ extended to the non-inverting input thereof. The gains of amplifiers $A_1$ and $A_2$ and the value of resistor 34 are such that the gain around the loop 27 is unity, and the inclusion of the integrator 33 makes that gain unity plus the integral of the signal (i.e. $1 + \int A_2$ output). In other words, the loop gain increases from unit (1) as the frequency of the signal applied to the input of operational amplifier $A_3$ in integrator 33 decreases. As this signal decreases in frequency, or, in fact, attains a DC offset value, that DC value serves to increase the value of the integral. Inasmuch as the feedback in loop 27 is of a degenerative nature, an increase in the value of the integrator gain increases the loop gain such that any DC offset which might otherwise bias the output of amplifier $A_1$ and/or amplifier $A_2$) is now removed. During rate-limiting when loop 27 is open, integrator 33 serves to hold the offset correction previously determined.

Figure 6B:
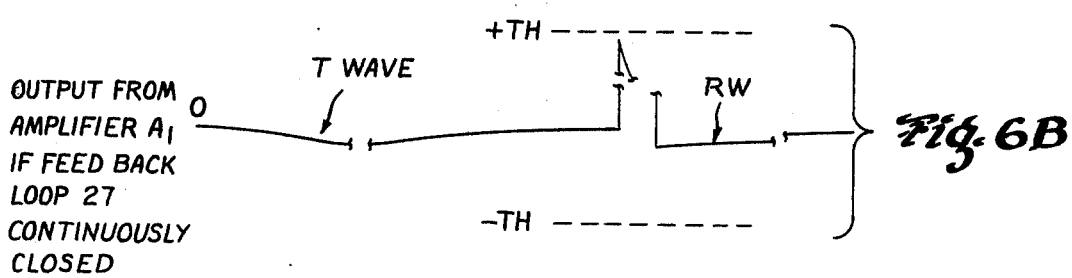
Figure 6C:
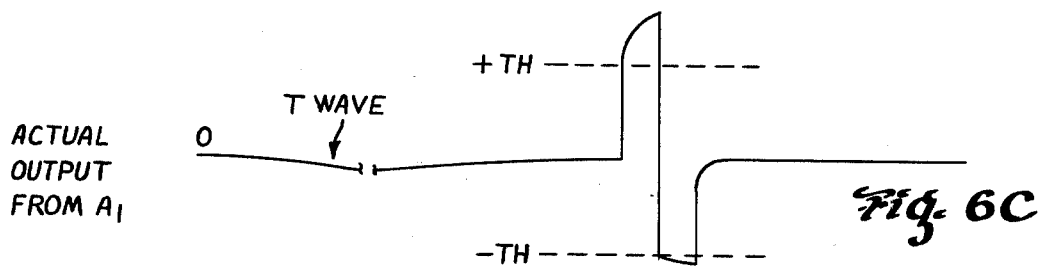
Figure 6D:
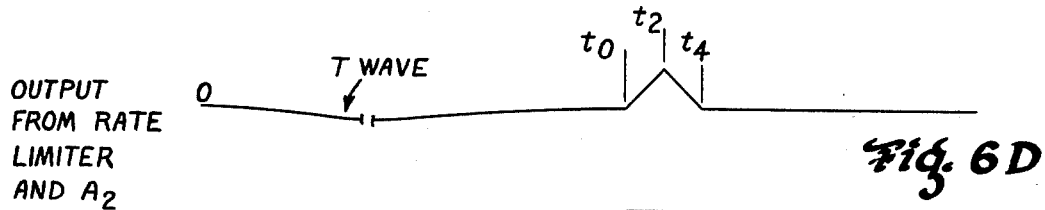

If rate-limiter 32 were not present in the feedback loop 27, that loop would continuously provide negative feedback and low-frequency rejection to the amplifier $A_1$ such that the output therefrom would be a stable, inverted replica of the small amplitude input signal provided by preamplifier $A_0$, as illustrated in FIG. 6B. However, the presence of rate-limiter 32 serves to, in essence, open the feedback loop 27 during the interval of rate-limiting caused by the spike portion of a pacer signal artifact. Although during this interval there may be some degree of negative feedback via loop 27 to the amplifier $A_1$ due to the ramping signal on capacitor 38, such feedback is not significant for the purpose of stabilizing the circuit and thus, the output of amplifier $A_1$ responds as illustrated in FIG. 6C. Instead of the unity gain under closed-loop conditions, as represented by the output appearing in FIG. 6B, the apparent gain of amplifier $A_1$ is now increased due to the removal of the negative feedback component at the input of amplifier $A_1$.

During operation with significant negative feedback being provided by a closed loop 27, the normal signal voltage excursion at the output of amplifier $A_1$ might typically be a small fraction of a volt. However, when this significant negative feedback is removed by the operation of a pacer spike on the rate-limiter 32, the signal at the output of amplifier $A_1$ will be substantially larger during the pacer spike portion. Further, the initial 1-2 milliseconds of the recharge waveform will be similarly amplified until rate-limiting ceases.

A voltage-level detector 40 connected to the output of amplifier $A_1$ responds to the increased magnitude of voltage appearing at the output of amplifier $A_1$ during the occurrence of the pacer discharge pulse portion for controlling the local feedback loop 28 and for also controlling the gate of a FET switch 41 associated with a follow-and-hold circuit 42 connected to the output of amplifier $A_2$. The voltage-level detector 40 is comprised of the emitter-base junctions of a pair of complementary (npn-pnp) transistors 43 and 44 respectively. The emitters of transistors 43 and 44 are connected in common to the output of amplifier $A_1$ and their bases are connected in common to one side of capacitor 30. The other side of capacitor 30 is connected to the input junction 26. A resistor 45 of high ohmic value (i.e. 4.7M) is connected in parallel across the emitter-base junctions of transistors 43 and 44.

During normal operation, the local feedback loop 28 is comprised only of the very high resistive path through resistor 45 and the capacitor 30 such that no significant feedback is provided. In effect, that loop might be considered as open, with the large resistance 45 being present essentially only to slightly reduce open-loop gain and thereby minimize the generation and occurrence of noise through the amplifier $A_1$. During this time, the negative feedback provided by loop 27 is such that the voltage appearing at the output of amplifier $A_1$ is less than that ($\pm$ Th in FIGS. 6B and 6C) required to forwardly bias the emitter-base junction of either transistor 43 or 44 such that they, in effect, comprise an open switch in the local feedback loop 28. However, with the occurrence of the leading edge of the pacer discharge pulse portion, slew rate limiter 32 operates to effectively disconnect feedback loop 27 and the voltage level at the output of amplifier $A_1$ increases greatly (either positively or negatively depending on the pacer polarity) to exceed either $+Th$ or $-Th$ and one or the other of the transistors 43 and 44 is forward-biased to provide a conductive path between the output of the amplifier $A_1$ and the capacitor 30, thereby effectively closing local feedback loop 28 and providing significant negative feedback to the input of amplifier $A_1$. It will be appreciated that because level detector 40 comprises a complementary pair of transistors, it is capable of responding to pacer signal artifacts of either polarity.

Throughout the duration of the discharge pulse portion of the pacer signal, the output of amplifier $A_1$ is fed back to its input through capacitor 30 in the manner of an integrator. Capacitor 30 serves to integrate the discharge pulse portion of the pacer signal, which integration is representative of and provides a measure of the charge delivered by the pacer for stimulating the patient's heart, as earlier discussed. The polarity of the charge developed on capacitor 30 is determined by the polarity of the discharge pulse portion of the pacer signal. During this charging of capacitor 30, the closed loop 28 serves to control the output of amplifier $A_1$ as seen in FIG. 6C.

At the completion of the discharge pulse portion of the pacer signal, the feedback loop 27 continues to be open for a brief period of time (i.e. $t_2-t_4$) and the voltage at the output of amplifier $A_1$ is, accordingly, of relatively large magnitude but now of the opposite polarity represented by the recharge waveform. At this time (i.e. $t_2$), that one of transistors 43, 44 which had been conducting is turned off and the other transistor is turned on to control the follow-and-hold circuit 42 as will be hereinafter described and also to control amplifier $A_1$ while capacitor 38 is recovering. Although this conduction by the formerly non-conducting one of the transistors 43, 44 results in some depletion of the charge accumulated on capacitor 30, such depletion is relatively slight inasmuch as the magnitude of the signal at the output of amplifier $A_1$ during the recharge waveform may be significantly less than that of the discharge pulse portion and further, both transistors 43, 44 become non-conducting quickly when rate-limiter 32 no longer operates to open loop 27 at time $t_4$ which may be about 2 milliseconds after the completion of the discharge pulse portion at $t_2$. Furthermore, the circuit element values may be prescaled to take this drop into consideration.

When transistors 43, 44 cease conduction, the feedback loop 28 will return to the near open-loop condition through resistor 45. However, now the capacitor 30, which has been charged proportionally to the charge delivered to the heart during the pacer spike portion, will begin to slowly discharge through the serial path represented by arrow 29 which includes the junction 26 at the input of amplifier $A_1$ and resistors 46 and 47 connected in series between the other end of capacitor 30 and the reference potential. The RC time constant of resistors 46, 47 and capacitor 30 is selected to generally correspond with the recharge time constant $T_C$ associated with the particular pacer and the patient. For instance, if recharge time constant $T_C$ is about 200 milliseconds, the time constant of resistors 46 and 47 and capacitor 30 should similarly be about 200 milliseconds. Resistor 47 is preferably variable to facilitate adjustment of the magnitude and the time constant of the signal waveform in discharge path 29 to substantially correspond with that of the recharge waveform generated by a particular pacer 18 and appearing at junction 26.

Inasmuch as the resistance R of one type of pacer may differ somewhat from that of another pacer, it is desirable to provide this feature of adjustability for scaling the magnitude and time constant of the tail suppression signal. Further, although the magnitude and decay constant of the tail suppression signal may not match exactly (oppositely) a particular pacer tail, it will reduce the resultant signal to an acceptable level, in most instances.

Figure 6E:
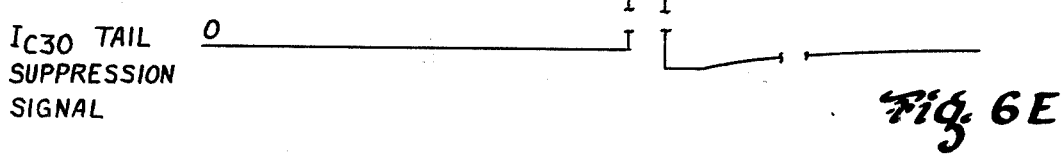

Inasmuch as junction 26 is connected to the inverting input amplifier $A_1$, the polarity of the charge stored on capacitor 30 during the feedback interval attending the discharge pulse portion of the pacer artifact is such that the signal current through capacitor 30 along discharge path 29 and appearing at junction 26 as represented by the waveform of FIG. 6E, is opposite in polarity to the recharge waveform then appearing at junction 26. Accordingly, because the current of the signal provided at junction 26 by the discharging capacitor 30 is opposite in polarity and comparable in both magnitude and decay time constant to the recharge waveform, the magnitude of such recharge waveform following summation with the recharge waveform suppression signal is considerably reduced and, in essence, suppressed at the input to amplifier A₁ and, accordingly, through rate-limiter 32 and amplifier A₂ to the output thereof.

A pair of parallel-connected, oppositely-poled diodes 48 are connected in parallel with capacitor 30 to speed the recovery of capacitor 30 from overload. Further, a normally-open switch 49 is connected in parallel with capacitor 30. While open, switch 49 has essentially no effect on the operation of the circuitry as hereinbefore described. However, when switch 49 is closed, as by manual actuation, capacitor 30 is essentially removed from both local feedback loop 28 and discharge path 29 with the resultant effect that the recharge waveform appearing at junction 26 is not suppressed and will appear at the output of amplifier A₂ for the purposes of analysis (i.e. polarity display), etc.

Referring to the follow-and-hold circuit 42, the output of amplifier A₂ is connected to the source electrode of FET 41, the drain electrode of which is connected in common with one end of resistor 50 and one end of capacitor 51. Resistor 50 extends serially to a low-pass filter 52, the output of which extends to a gain control amplifier 53 which, in turn, controls a light-emitting diode (not shown) associated with optical coupling element 54. Optical coupling element 54 serves to isolate the aforementioned circuitry from the heart-rate meter 12 and the display apparatus 14 to which its output is either directly or indirectly connected. The capacitor 51 extends between the drain electrode of FET 41 and the reference potential for tracking and storing the potential appearing on the drain electrode.

A self-restoring drive or biasing network 95 comprised of switching diode 55, zero-biasing resistor 56, diode-biasing resistors 57 and 58 and coupling capacitor 59 is connected to the gate electrode of FET 41 for maintaining the FET in a normally-conducting mode and responding to a negative pulse coupled thereto through capacitor 59 for temporarily switching the FET into non-conduction. The resistor 57 is driven by the output of amplifier A₂ so that diode 55 is biased more positively than the source of FET 41.

Figure 6F:
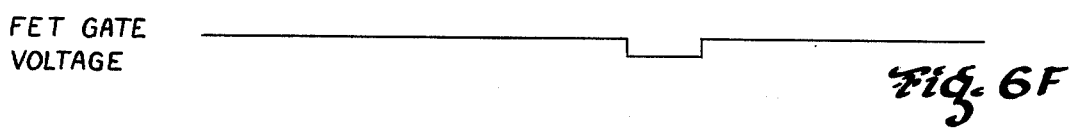

With FET 41 normally biased into conduction, the signal appearing at the output of A₂ is extended through the follow-and-hold circuitry 42 and subsequently through optical coupler 54 to display 14 and/or heart-rate meter 12. However, it will be appreciated that in the interval during which rate-limiting occurs (i.e. $t_0$–$t_4$), the rate-limited voltage appearing on capacitor 38 and illustrated as a triangular stump in FIG. 6D may, itself, be capable of stimulating an erroneous response by the heart-rate meter 12. This situation arises because although the slope of the rate-limited signal must be low enough to effectively open the feedback loop 27, it must not be so low as to suppress validly occurring QRS waveforms. Therefore, the output of amplifier A₂ is disconnected from the follow-and-hold capacitor 51 and resistor 50 for the interval during which the rate-limited triangular stump appearing in FIG. 6D exists. This is accomplished by reverse-biasing the gate electrode on FET 41, as illustrated by the control voltage waveform in FIG. 6F.

The relatively negative or reverse-biased control voltage applied to the gate of FET 41 is determined by the level detector 40 which operates through transistor 60 to generate a negative pulse or step which, in turn, is coupled through capacitor 59 to the self-restoring bias circuit 95 associated with the gate of FET 41. The collector of transistor 43 is connected to the cathode of an isolating diode 61 having its anode connected to a junction 62. Similarly, the collector of transistor 44 is connected through a transistorized inverter, generally represented by arrow 63, to the junction 62. The base of transistor 60 is connected through current-limiting base resistor 64 to the junction 62. The quiescent potential at junction 62 is +V which biases transistor 60 into non-conduction. The collector of transistor 60 is connected to the reference potential and a capacitor 71 is connected between the collector and the junction between resistors 65 and 66. An optical coupling unit 70 has its primary side (i.e. an LED, not shown) connected in the emitter circuit of transistor 60 in series with a current-limiting resistor 68 and resistor 65.

When either of transistors 43, 44 of level detector 40 begins conducting with the occurrence of a pacer discharge pulse, the voltage at junction 62 drops, resulting in turn-on of transistor 60 and a resultant drop in the potential at its emitter. The capacitor 59 is connected at one end to the emitter of transistor 60 and, accordingly, serves to AC couple the resulting negative spike or step to the self-restoring drive circuit 95 to thereby bias FET 41 into non-conduction. Following the drop in voltage on the emitter of transistor 60, the capacitor 59 will begin to recharge with a time constant determined essentially by resistor 57 and its own capacitance until such time as forward-bias returns to the gate of FET 41 and it resumes conduction. This interval may be about 8–10 milliseconds which is normally longer than the rate-limited interval represented by the triangular stump in FIG. 6D.

The capacitor 71 is provided to insure that transistor 60 does not briefly return to non-conduction in the brief interval between turn-off of one of transistors 43, 44 and the turn-on of the other. Were transistor 60 to briefly return to non-conduction, there would appear a positive voltage step at its emitter which would be coupled through capacitor 59 to briefly return FET 41 to conduction and thereby pass the peak-value of the rate-limited signal through circuit 42. Instead, the RC time constant established by resistor 65 and capacitor 71 is such that the transistor 60 does not return to non-conduction during the brief interval of switching of the transistors in level detector 40. When the response of rate-limiter 32 to a pacer signal artifact has been completed and both transistors 43, 44 of level detector 40 return to non-conduction, the transistor 60 similarly returns to non-conduction resulting in the generation of a positive step which is AC coupled through capacitor 59 to return FET 41 to its normally conducting condition.

Figure 6G:
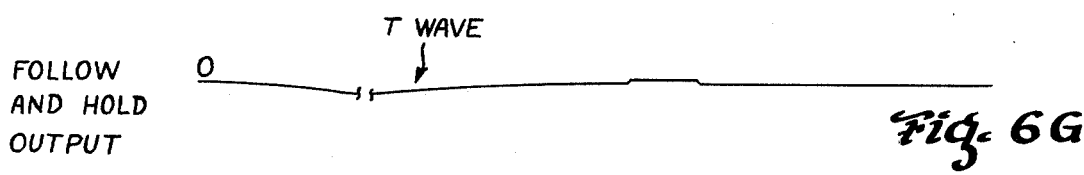

The result of disconnecting FET switch 41 during the rate-limiting interval is illustrated in FIG. 6G wherein the voltage appearing on capacitor 51 at the moment switch 41 becomes non-conducting is only slightly greater than the base line value and, accordingly, remains as such throughout the interval of non-conduction of the FET switch. Thus, the follow-and-hold circuit 42 removes the rate-limited stump from the pacer signal artifact, and the recharge waveform suppression circuit including capacitor 30 serves to suppress the appearance of the following recharge waveform such that substantially only the PQRST complex is presented to optical coupler 54. The low-pass filter 52 serves to remove any remaining switching transients and sets the upper limit to the bandwidth of amplifier 11.

The optical coupler 70 associated with switch 60 serves to generate a trigger signal each time transistor 60 begins conduction in response to detector 40 detecting the presence of a pacer signal artifact. This trigger signal is extended via line 72 to the trigger input of a one-shot multivibrator 73 for generating a pacer tag signal of possibly ten milliseconds duration for extension via line 74 to an input of summer 75. The other input to summer 75 is obtained, via line 76, from the non-isolated output of optical coupler 54 on which appears the sensed ECG signal having the pacer discharge pulse portion and the recharge waveform portion of a pacer signal artifact suppressed. The pacer tag appearing on line 74 is summed with the signal appearing on line 76 to provide an output signal on line 77 which comprises any PQRST complex as well as a pacer tag to indicate the occurrence and timing of a pacer signal artifact. The signal on line 77 is extended to the display 14.

If it is desired that display 14 present only the signal appearing on line 76, whether with or without the pacer artifact signal suppressed, the pacer tag may be deleted from the display by opening normally-closed switch 69 connected in series between resistor 68 and transistor 60. This positioning of switch 69 allows the "stump" of FIG. 6D to appear as an indication of the pacer pulse polarity. Switch 69 might instead be connected to gate the one-shot 73 directly, thereby permitting the "stump" to also be suppressed on line 76. Switches 49 and 69 might be ganged.

It will be appreciated that instead of the embodiment illustrated in FIG. 5, it would be possible to extend the input from the patient and the input of the general feedback represented by loop 27 to a non-inverting input of amplifier $A_1$ and to further replace the non-inverting integrator 33 with an inverting integrator and to additionally provide a further gain controlling (resistive) feedback loop extending from the output of amplifier $A_2$ to the inverting input of amplifier $A_1$. The gain of the closed loop may be easily controlled by the resistance in the separate feedback path, but in either embodiment, the effect is substantially the same.

The invention may be embodied in other specific forms without departing from the spirit or essential characteristics thereof. The present embodiments are, therefore, to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. In an ECG amplifier for receiving a sensed ECG signal from a patient and including signal suppression means for suppressing the pacer discharge pulse portion and the recharge waveform portion of a heart pacer signal artifact appearing in the sensed ECG signal, the improvement wherein said recharge wave suppression means comprises:

means for measuring the quantity of electrical charge in the pacer discharge pulse portion of a pacer signal artifact in the sensed ECG signal, said quantity of discharge being representative of the quantity of electrical recharge of said recharge waveform portion of the respective said pacer signal artifact;

means responsive to said measure of electrical discharge of said discharge pulse portion for generating a recharge waveform suppression signal of opposite polarity to said recharge waveform portion of the pacer signal artifact;

means for adjusting the time constant of said suppression signal to cause the time constant of said suppression signal to correspond to the time constant of said recharge waveform; and means for arithmetically summing the recharge waveform suppression signal with the recharge waveform portion of said pacer signal artifact so as to reduce said recharge waveform portion of the pacer signal artifact.

2. The amplifier of claim 1 wherein said means for measuring the quantity of electrical charge of said discharge pulse portion of a said pacer signal artifact comprises an operational amplifier having an input and an output, the sensed ECG signal being connected to said amplifier input, and electrical energy-storing means connected in a local feedback loop between said output and said input of said operational amplifier means at least for the interval during which a said pacer discharge pulse portion exists for integrating said sensed ECG signal applied to said operational amplifier input, the integral of said sensed ECG signal over said interval of pacer discharge pulse portion existence being a measure of the electrical discharge of the respective said pacer discharge pulse portion.

3. The amplifier of claim 2 wherein said recharge waveform suppression signal generating means comprises means for utilizing said energy stored by said storing means during said integration to generate a suppression current of decreasing magnitude substantially immediately following said discharge pulse portion of said pacer signal artifact, the initial magnitude and rate of decay of said suppression current being determined by a resistance-capacitance circuit having said stored energy applied thereto, said suppression current being extended to said operational amplifier input and being of the opposite polarity to the current of said recharge waveform signal portion of the sensed ECG signal applied to said operational amplifier input thereby to have a mutally cancelling effect.

4. The amplifier of claim 3 wherein the recharge waveform portion of a pacer signal artifact has a particular RC decay constant and said resistance-capacitance circuit of said recharge waveform suppression signal generating means is scaled such that said recharge waveform suppression signal substantially cancels said recharge waveform signal.

5. The amplifier of claim 3 wherein said local feedback loop including said energy-storage means is normally disconnected from significant feedback relationship with said operational amplifier and is selectively controllable for connection into significant feedback relationship with said operational amplifier, said feedback arrangement including controllable normally-open switch means in series with said energy-storing means, said switch means being responsive to the output of said operational amplifier exceeding a predetermined amplitude level for connecting said local feedback arrangement in significant feedback relationship with said operational amplifier.

6. The amplifier of claim 5 wherein said energy-storage means comprises capacitance means and said capacitance means comprises part of said resistance-capacitance circuit.

7. The amplifier of claim 5 wherein said means for connecting said local feedback arrangement including said energy-storing means into significant feedback relationship with said operational amplifier further comprises a second feedback loop normally operatively connected between said output and said input respectively of said operational amplifier for providing negative feedback to said operational amplifier input to limit the amplitude of the signal appearing at the output of said operational amplifier to values normally less than said predetermined amplitude level required for response of said switch means, said second feedback loop including rate-limiting means, said rate limiting means acting to reduce the feedback of said second feedback loop in response to signals at the output of said operational amplifier exceeding a predetermined rate of change, thereby enabling said operational amplifier output signal to exceed said predetermined amplitude level required for response of said switch means.

8. The amplifier of claim 7 wherein said normally open switch means comprises a pair of oppositely-poled, parallel-connected, unidirectionally-conducting semiconductors.

9. The amplifier of claim 8 wherein said pair of semiconductor switches is connected between the output of said operational amplifier and said energy-storing means.

10. The amplifier of claim 9 including resistance means of relatively large ohmic value connected in parallel with said semi-conductor switches, the ohmic value of said resistance means being sufficiently large to minimize noise on the signal appearing at the output of said operational amplifier when both switches of said pair are open and substantially non-conducting.

11. The amplifier of claim 7 wherein said predetermined rate of amplitude change is normally not exceeded by the PQRST complex of said ECG signal nor by said recharge waveform portion of a said pacer signal artifact and is exceeded by said pacer discharge pulse portion.

12. The amplifier of claim 11 wherein said predetermined rate of amplitude change is additionally normally not exceeded by muscle artifact noise.

13. The amplifier of claim 7 wherein said second feedback loop also includes second integrating means operatively connected in series with said rate-limiting means thereby to minimize D.C. offset.

14. The amplifier of claim 13 including output means, and means operatively connected to said second feedback loop, to the output of said operational amplifier and to said output means for selectively controlling extension of the signal on said second feedback loop to said output means, said control means being responsive to the operational amplifier output signal being less than a particular amplitude level for extending the signal on said second feedback loop to said output means and being responsive to the operational amplifier output signal being greater than said particular amplitude level for blocking extension of the signal on said second feedback loop to said output means.

15. The amplifier of claim 14 wherein said control means is connected to said second feedback loop effectively at the output of said rate-limiting means and includes gated follow-and-hold means, and said particular amplitude level which is the same as said predetermined amplitude level which controls said local feedback loop.

16. In an ECG amplifier for receiving a sensed ECG signal from a patient and including signal suppression means for suppressing at least the discharge pulse portion of a heart pacer signal artifact possibly appearing in the sensed ECG signal, the improvement wherein said suppression means comprises:

amplification means having an input and an output, the sensed ECG signal being connected to said input;

a feedback loop between said output and said input respectively of said amplifying means for providing negative feedback to said amplifying means input, said feedback loop including signal integrating means to minimize the DC offset in the signal at said amplifying means output and rate-limiting means, said rate-limiting means acting to reduce the feedback of said feedback loop in response to signals at the output of said amplifying means exceeding a predetermined rate-of-change, level-detection means operatively connected to the output of said amplifying means for providing a control signal substantially only while the amplitude of the signal appearing at the output of said amplifying means exceeds a threshold level; and gated follow-and-hold means operatively connected to a point in said feedback loop and being normally operative to provide an output signal voltage which normally tracks the signal appearing at said point in said feedback loop and being responsive to said control signal from said level-detecting means for preventing said output signal voltage from tracking said signal at said point in said feedback loop and for holding the last said output signal voltage, whereby said output signal voltage from said follow-and-hold means has at least said discharge pulse portion of a said pacer signal artifact removed therefrom.

17. The ECG amplifier of claim 16 wherein said integrating means is in series with said rate-limiting means.

18. The ECG amplifier of claim 17 wherein said point in said feedback loop to which said gated follow-and-hold means is operatively connected is intermediate the output of said rate-limiting means and said input of said amplification means.

19. The ECG amplifier of claim 18 wherein said predetermined rate of change of said rate-limiting means corresponds with a predetermined rate of change of signal amplitude, said predetermined rate-of-change normally not being exceeded by the PQRST complex of said ECG signal nor by muscle artifact noise and normally being exceeded by said pacer discharge pulse portion of a pacer signal artifact.

20. The ECG amplifier of claim 16 wherein said threshold level of said level-detection means comprises a pair of substantially equal voltages of opposite polarities.

* * * * *